United States Patent [19]

Bottlik

[11] Patent Number: 5,417,670

[45] Date of Patent: May 23, 1995

[54] PUNCTURE NEEDLE DEVICE, MAINLY FOR A CLOSED SYSTEM INTRODUCTION OF A CATHETER INTO A BLOOD VESSEL

[76] Inventor: Gyula Bottlik, Tárogató u. 96/D.11.8, H-1021 Budapest, Hungary

[21] Appl. No.: 204,353
[22] PCT Filed: Sep. 11, 1992
[86] PCT No.: PCT/HU92/00035
  § 371 Date: May 20, 1994
  § 102(e) Date: May 20, 1994
[87] PCT Pub. No.: WO93/04723
  PCT Pub. Date: Mar. 18, 1993

[30] Foreign Application Priority Data

Sep. 12, 1991 [HU] Hungary ................. 2931/91

[51] Int. Cl.⁶ ............................................. A61M 5/00
[52] U.S. Cl. .................................. 604/264; 604/283; 604/284
[58] Field of Search ................ 604/264, 283, 284, 164, 604/167, 158, 256, 280

[56] References Cited

U.S. PATENT DOCUMENTS

| 3,574,306 | 4/1971 | Alden . | |
|---|---|---|---|
| 3,585,996 | 6/1971 | Reynolds et al. . | |
| 3,910,272 | 10/1975 | Forberg . | |
| 3,920,013 | 11/1975 | Bodzin . | |
| 4,224,943 | 9/1980 | Johnson et al. . | |
| 5,176,697 | 1/1993 | Hasson et al. | 604/174 X |
| 5,207,648 | 5/1993 | Gross | 604/264 X |
| 5,250,040 | 10/1993 | Parks et al. | 604/174 X |
| 5,290,244 | 3/1994 | Moonka | 604/164 |
| 5,300,046 | 4/1994 | Scarfone et al. | 604/264 |
| 5,350,362 | 9/1994 | Stouder, Jr. | 604/167 |

FOREIGN PATENT DOCUMENTS 355190  2/1980  Austria .

Primary Examiner—John D. Yasko
Attorney, Agent, or Firm—Spencer, Frank & Schneider

[57] ABSTRACT

A puncturing needle device for introducing a catheter into a blood vessel, including a body; a catheter duct passing through the body for guiding a catheter therethrough; a syringe duct extending in the body from a syringe duct opening provided in the body and merging into the catheter duct at a merging location between opposite ends thereof for receiving a syringe introducible into the syringe duct through the syringe duct opening; and a needle having a throughgoing inner passage and an end attached to the body to communicate with the catheter duct. The inner wall surface of the catheter duct and the inner wall surface of the needle passage form a smooth transition from the catheter duct to the passage. The syringe duct and the passage are oriented to one another at an oblique angle. There is further provided a lock element positioned in the catheter duct between the merging location and that end of the catheter duct which is distal from the needle passage.

9 Claims, 2 Drawing Sheets

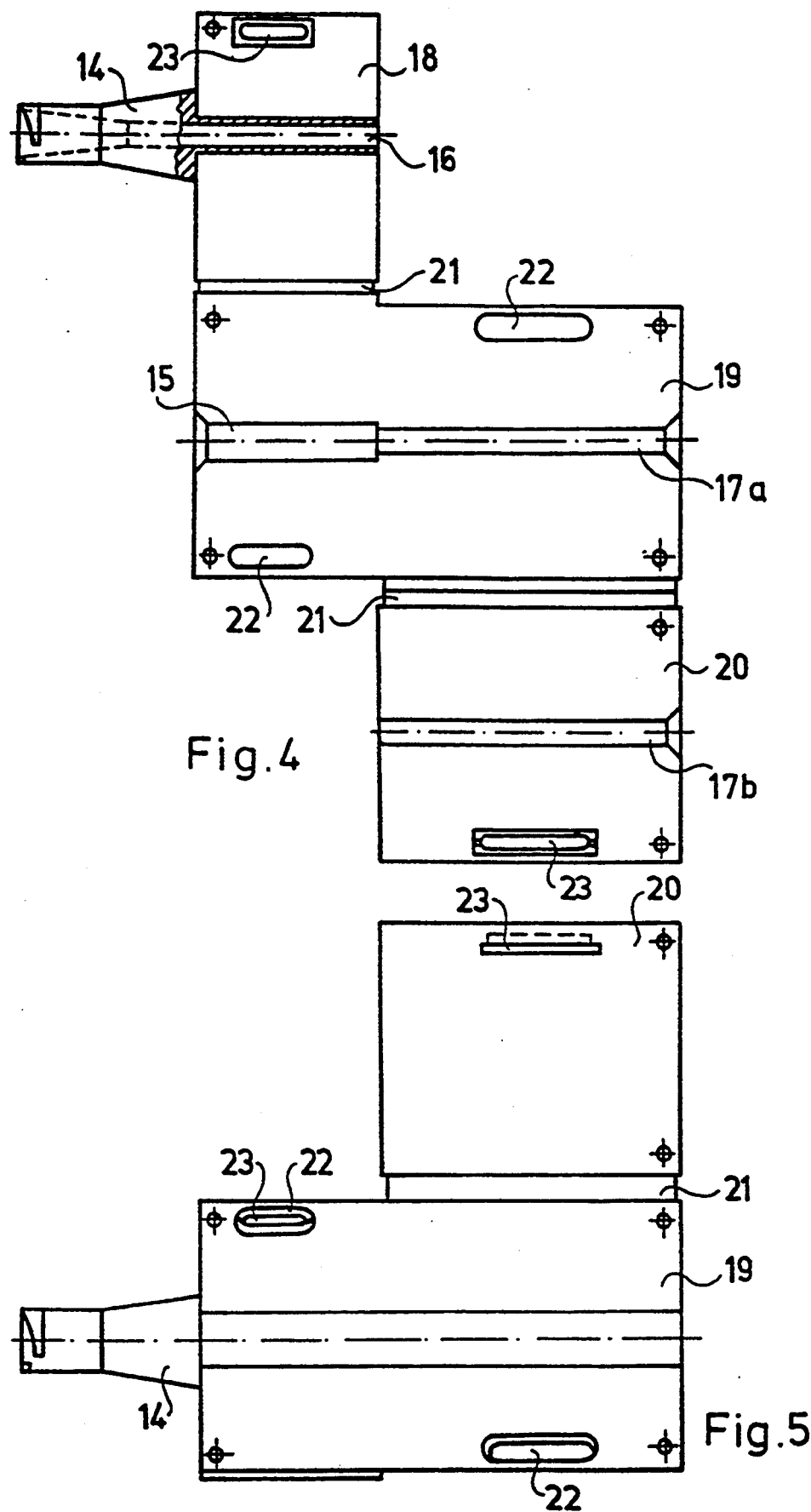

PUNCTURE NEEDLE DEVICE, MAINLY FOR A CLOSED SYSTEM INTRODUCTION OF A CATHETER INTO A BLOOD VESSEL

BACKGROUND OF THE INVENTION

This application is a 371 of PCT/H092/00035, filed Sep. 11, 1992.

The present invention relates to a puncture needle device, mainly for a closed system introduction of a catheter into a blood vessel, consisting of a needle and a body. The device can also be used for introducing pacemaker electrodes, guide wires or the like.

Haemodialysis, blood transfusion and replacement, or parenteral nutrition of patients in serious condition is generally carried out through catheters introduced into a central vein of the patient. Especially important is an appropriate indroduction of-such catheters into the great veins near to the heart of the patient, during permanent administration of drugs, nutritional fluids, blood etc.

Catheters may be punctured into a blood vessel in different ways.

When applying a so called Branüle-type device, the catheter surrounds the puncture needle as a sleeve and the needle introduced into the blood vessel is guiding said sleeve which is then also introduced into the blood vessel. Finally, the needle is pulled out of the catheter.

This method of puncturing can only be applied in a sterilized room as the introduction of the catheter is carried out in an open wound.

Another known method is the so-called Seldinger-method, wherein the syringe is removed from the needle after it has been punctured into the vein and a guiding wire is introduced into the vein through the passage of the needle. Thereafter, the needle is removed from the wire and the catheter is introduced into the vein guided by the same wire.

The advantage of this method is that a rather thick catheter can be introduced into a relatively small opening on the vein. The drawback is however, that the system is opened by removing the syringe and, accordingly, there is a growing danger of infection.

Furthermore, the point of the needle often slips out of the vein during removing the syringe and introducing the wire, which can cause additional injuries. Extravasations can also occure, wich make diffucult or even impossible to carry out further punctures.

Yet another method is known, wherein a relativly thick needle is punctured into the blood vessel and the catheter is introduced directly through the passage of the needle, after the syringe has been removed. Thereafter, the needle is pulled out of the vein and removed from the catheter (which is possible only if there is no flange at the end of the catheter).

Disadvantage of this method is that the system becomes opened when the syringe is removed and that the point of the needle easily slips out of the vein, as it has been explained in connection with the Seldinger-method.

The weak point of all the known methods is the difficulty of introduction of the catheter. Due to this, the puncture needle may accidently be pulled out and infection would be a real danger in such an open system. Generally, the danger of pulling out the needle is about 20–30%, even if it is used by a skilled person.

Another problem is fixing the outer end of the catheter. For this purpose catheter holders made of several parts are generally used (see e.g. U.S. Pat. No. 4,149,535). The use of such catheter holders is generally rather difficult, because all the parts should be mounted at the end of the catheter.

SUMMARY OF THE INVENTION

The object of the present invention is therefore to provide a puncture needle device for eliminating the drawbacks of the prior art and to enable a safe introduction and fixing of catheters and the like into blood vessels, in closed system.

The puncture needle device according to the invention consists of a needle and a body, wherein said body is provided with two tubes, each being arranged at the end of a duct. A catheter duct is connected to the passage of the needle via smooth surface, meanwhile a syringe duct includes an oblique angle with the passage of the needle. The catheter duct contains a lock element between the catheter tube and the intersection of the ducts.

The catheter duct is preferably straight and coaxial with the passage of the needle. The syringe duct can also be straight, but it includes an acut angle with the catheter duct.

According to another embodiment, both the catheter duct and the syringe duct are arcuate.

The body of the needle device is provided with a flat grip.

The lock element in the catheter duct may be a valve or a membrane.

The needle may be provided with a protecting cover.

The device is preferably provided with a catheter holder consisting of plates, wherein the lower part of the holder is a single plate and the upper part thereof is made of two foldable plates. The foldable plates may be arranged on two opposite sides of the lower plate, displaced with respect to each other. The plates are connected to each other by elastic bands.

It should be noted that a catheter holding device provided with a side tube has already been disclosed in the U.S. Pat. No. 4,149,535. This device is, however, a plastic body and a needle can be inserted into said body in a way that a forward end of the needle projects from the forward most end portion of the body. The body is introduced into the blood vessel after the needle has been punctured therein. A catheter is introduced through the side tube first into the main passage of the body and further into the vein. The central tube of the body receives then connection from an intraveneous system such as system for the transfusion of blood.

Thus, the catheter holding device is used for a number of dual functions, e.g. the simultanious measurement of the central venous pressure and transfusion of liquids into the blood vessel.

The above catheter holding device, however, does not enable a reliable closed system introduction of a catheter, though it is provided with two branch tubes. The reason thereof is that the body is not suitable for puncturing on the one hand, and, it has the same drawbacks as the prior art solutions on the other hand.

It is a further disatvantage that the introduction of the catheter is carried out through the side tube, which is rather difficult because of the sudden change of direction of the introduction. For the same reason, the friction between the catheter and the body is also rather high. An increasing friction is also caused by the resilient sealing material.

According to the invention, the introduction of the catheter is carried out in a closed system all the time, because the catheter duct is closed and the syringe need not be removed from the syringe duct. This fact goes at the same time with the advantage, that the number of steps needed for the puncturing is lower than usual.

The syringe and the catheter are already in the tubes when puncturing occurs and the syringe need not be removed when blood is appearing. The only steps needed are to open the lock element and to introduce the catheter.

The invention is based on the recognition that the introduction of a catheter, pacemaker electrode or guiding wire can be carried out the most safe way and the danger of accidentally pulling out the needle from the vein can be avoided with the greatest chance, when the minimum number of steps should be carried out after the puncture needle has been introduced into the vein. Such steps are e.g. removing the syringe and replacing it by the catheter, electorde or guiding wire. If therefore, these steps can be avoided or carried out before puncturing or after introducing the catheter, introducing the catheter can be carried out the most safe way.

Accordingly, if the needle device is provided with a syringe tube and a catheter tube, the catheter can be placed into the catheter tube before and the syringe can be removed after the introduction of the catheter, i.e. no step should be carried out between puncturing and introducing the catheter. So the danger of accidendal pulling out the needle can be minimized.

These and other advantages of the device according to the invention will be explained more in details by way of examples with reference to the accompanying drawing.

BRIEF DESCRIPTION OF THE DRAWINGS

FIG. 4 is a catheter holding device in an opened position and

FIG. 5 is the catheter holding device of FIG. 4 when closed.

DESCRIPTION OF THE PREFERRED EMBODIMENTS

Figure 2:
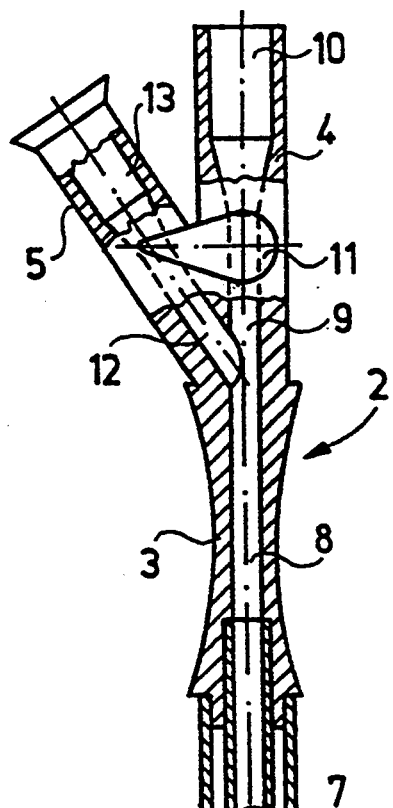
FIG. 2 is a side view of a part of the embodiment shown in FIG. 1.
Figure 2:
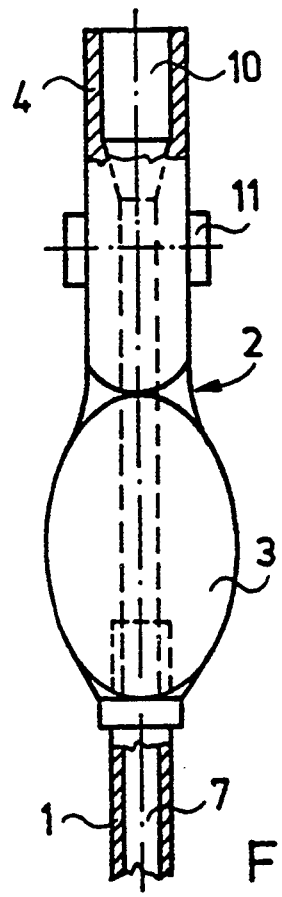
Figure 1:
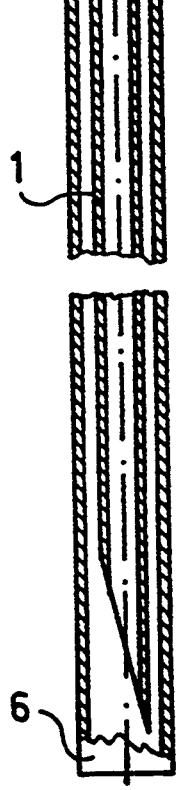
FIG. 1 is an embodiment of the invention, partly in section.

Referring to the drawings, FIGS. 1 and 2 show a first embodiment of the device according to the invention. Needle 1 is provided with a body 2. The lower part of said body 2 has a flat shape and can be used as a grip 3. On the upper part of body 2 there are two tubes: catheter tube 4 and syringe tube 5. The needle 1 itself is surrounded by a protecting cover 6 which should be removed before using it.

The passage 7 of the needle 1 is coaxial with the central bore 8 of the body 2 as well as with the catheter duct 9 of the catheter tube 4. Accordingly, said passage 7, central bore 8, and catheter duct 9 produce a straight passage of uniform diameter.

At the end of the catheter duct 9 there is a bore Between the bore 10 and the catheter duct 9 is a frustoconical passage. Just below said frustoconical passage, there is a lock element 11 in catheter duct 9. The lock element 11 in this embodiment is a simple valve.

A syringe duct 12 is opens into the central bore 8 of the body 2 at the mouth of catheter duct 9. Catheter duct 9 and syringe duct enclose an acute angle with each other and they are of the same diameter.

There is a bore 13 in the syringe tube 5 at the end of the syringe duct 12. Between bore 13 and syringe duct 12 there is a frustoconical passage, which can receive a syringe.

Figure 3:
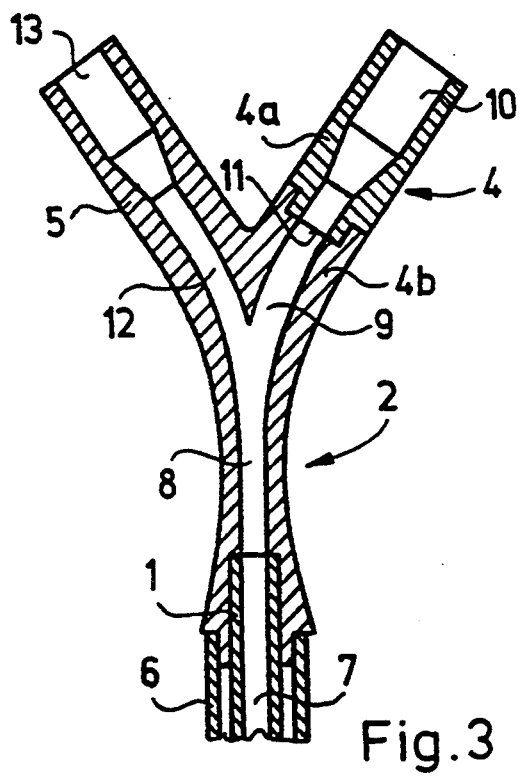
FIG. 3 is the upper part of another embodiment partly in section.

FIG. 3 shows the upper part of another embodiment of the invention. Here, the passage 7 of the needle, the central bore 8 of the body 2 and the catheter duct 9 do not produce as straight passage but they have an arcuate shape with a smooth surface, which means that there is no sudden change in the direction or diameter of the passage 7 in order to enable a smooth introduction of the catheter into the passage 7 of the needle 1.

The syringe duct 12 and the central bore 8 of the body 2 produce a similar passage being symmetrical with respect to the catheter duct 9.

The locking element 11 in the catheter duct 9 is not a valve in this embodiment but a membrane which can be punctured by the end of the catheter. The membrane is held by parts 4a and 4b of the catheter tube 4. Part 4a has a threaded end portion fitting into the inner thread of part 4b. There is a sealed connection between parts 4a and 4b.

FIGS. 4 and 5 show a catheter holder according to the invention. The catheter holder consists of plates 18, 19 and 20 provided with an infusion sleeve 14, a fixing sleeve 16 and grooves 15, 17a and 17b. The plates 18, 19 and 20 are connected to each other by elastic bands 21. Fixing the folded plates 18, 19 and 20 can be achieved by snap fasteners 22 and 23.

FIG. 4 shows the catheter holder in an open-position.. Upper plates 18 and 20 are arranged on two opposite sides of lower plate 19. Plates 18 and 20 are offset with respect to each other.

Plate 18, infusion sleeve 14 and fixing sleeve 16 are integrally formed of a single piece and groove 15 in plate 19 is shaped to receive sleeves 14 and 16.

FIG. 5 shows the catheter holding device when plate 18 is closed to base plate 19. In this position, groove 15 is fixing the end of the catheter in fixing sleeve 16. Grooves 17a and 17b surround a further part of the catheter and do not allow the passage of the catheter to bend or buckle.

The device according to the invention can be used as follows.

Cover 6 is removed from needle 1 and a syringe is inserted into syringe tube 5. Then, the person using the device, holds grip 3 with one hand, pulls the plunger of the syringe with the other hand and, at the same time, puncturing is carried out. In the next step, the syringe is released and lock element 11 is opened with the free hand. This means turning the valve at 90° in the embodiment of FIGS. 1 and 2, or puncturing the membrane with the end of the catheter if embodiment according to FIG. 3 is applied.

In this way, the catheter slides through the catheter duct 9 into the passage 7 of the needle 1 and further into the blood vessel.

When the catheter has been entered into the blood vessel, the needle device will be pulled out from the catheter. Infusion sleeve 14 will then be fixed at the end of the catheter and plate 18 will be bent to plate 19. Snap fastener 23 and snap hole 22 will then hold plates 18 and 19 fixed together. In the next step, plate 20 will also be bent to plate 19 and a further part of the catheter will be fixed between grooves 17a and 17b. The closed catheter holder will then be fixed to the patient's skin and an infusion device will be coupled to infusion sleeve 14.

In the above, the use of the device according the the invention has been explained in the case of catheter introduction. It is obvious for anybody skilled in the art, that introduction of pacemaker electrodes or guide wires can be carried out in a the same way. The device is suitable for carrying out the Seldinger method as well.

It should be noted, however, that the system will be opened when the needle device is removed from an electrode or a guiding wire and, accordingly, the step should then be carried out in sterilized room.

The main advantage of the device according to the invention is that no change of grip has to be carried out during introduction of a catheter, electrode or guide wire, the syringe does not need to be removed and the catheter should not be inserted into device, during puncturing. No blood can leave the system during operation and the catheter can be introduced in the blood vessel with a minimum number of steps to be carried out.

Due to these circumstances, there is a considerably reduced danger that the needle leaves the blood vessel before finishing the operation. Entering the catheter is carried out in a completely closed system and therefore the danger of infection is actually avoided. Thus, the steps may even be carried out without steril gloves, for instance in emergency cases.

A further advantage of the device according to the invention is that the length of the rigid part of the system is smaller than that of the prior art devices. This fact makes the operations during puncturing easier, which is of great importance, especially in the case of puncturing the vein subclavia.

On the other hand, connecting, guiding and fixing the free end of the catheter can be carried out with the catheter holder according to the invention quickly, simply and safely.

The device according to the invention makes easier the work of the doctor during introduction of a catheter and, at the same time, considerably reduces the risk to the patient.

Still a further advantage of the device according to the invention is that any catheter (single or multiple human, etc) can be introduced into any vein (subclavia, jugularis interna or externa, greater peripheral vein) or even into different artheries (if Seldinger-technics is applied). The device can be produced as a conventional or disposable one.

While embodiment of device according to the invention have been illustrated and described herein in considerable detail, the invention is not to be considered limited to the embodiments. Other adaptations, modifications and uses of the invention may occur to those skilled in the art to which the invention relates and it is intended to cover all such adaptations, modifications and uses which come within the scope of the appended claims.

I claim:

1. A puncturing needle device for introducing a catheter into a blood vessel, comprising
    (a) a body;
    (b) means defining a catheter duct passing through said body for guiding a catheter therethrough; said catheter duct having an inner wall surface and opposite first and second ends;
    (c) means defining a syringe duct extending in said body from a syringe duct opening provided in said body and merging into said catheter duct at a merging location between said first and second ends thereof for receiving a syringe introducible into said syringe duct through said syringe duct opening;
    (d) a needle having a throughgoing inner passage and an end attached to said body at a second end of said catheter duct; said passage having an inner wall surface; said inner wall surface of said catheter duct and said inner wall surface of said passage forming a smooth transition from said catheter duct to said passage; said syringe duct and said passage being oriented to one another at an oblique angle; and
    (e) a lock element positioned in said catheter duct between said merging location and said first end of said catheter duct.

2. The puncturing needle device as defined in claim 1, wherein said catheter duct is straight and is in an axial alignment with said passage.

3. The puncturing needle device as defined in claim 1, wherein said catheter duct and said syringe duct are oriented at an acute angle to one another relative to a direction pointing from said first end toward said second end of said catheter duct.

4. The puncturing needle device as defined in claim 3, wherein said syringe duct is straight.

5. The puncturing needle device as defined in claim 3, wherein said syringe duct is arcuate.

6. The puncturing needle device as defined in claim 1, wherein said body includes flattened outer surface portions constituting a grip.

7. The puncturing needle device as defined in claim 1, wherein said lock element includes a shutoff valve for closing or opening said catheter duct.

8. The puncturing needle device as defined in claim 1, wherein said lock element includes a pierceable membrane.

9. The puncturing needle device as defined in claim 1, further comprising a removable protective cover surrounding said needle.

* * * * *